United States Patent [19]

Asai

[11] 4,239,042
[45] Dec. 16, 1980

[54] CATHETER PLACEMENT SYSTEM
[75] Inventor: Kiyoshi Asai, Kamakura, Japan
[73] Assignee: Dow Corning K.K., Tokyo, Japan
[21] Appl. No.: 18,214
[22] Filed: Apr. 5, 1979
[51] Int. Cl.³ .............................................. A61M 5/00
[52] U.S. Cl. .................................. 128/214.4; 128/348
[58] Field of Search .................... 128/214.4, 221, 348, 128/218 N, 349 R, DIG. 16

[56] References Cited

U.S. PATENT DOCUMENTS

| 3,856,009 | 12/1974 | Winnie | 128/214.4 |
| 3,867,937 | 2/1975 | Schwartz | 128/221 |
| 4,068,659 | 1/1978 | Moorehead | 128/214.4 |

Primary Examiner—John D. Yasko
Attorney, Agent, or Firm—Max J. Kenemore

[57] ABSTRACT

In a through-the-cannula catheter placement system, a catheter is used which comprises a body portion and a tip portion at one end of the body portion. The body portion has a double-wall structure. The outer wall is a tube of pliable, nonthrombogenic material. The inner wall is a reinforcing tube of a material having sufficient resilience to avoid collapse during use. The tip portion is also made of a pliable nonthrombogenic material. The tip may be an extension of the outer wall.

6 Claims, 9 Drawing Figures

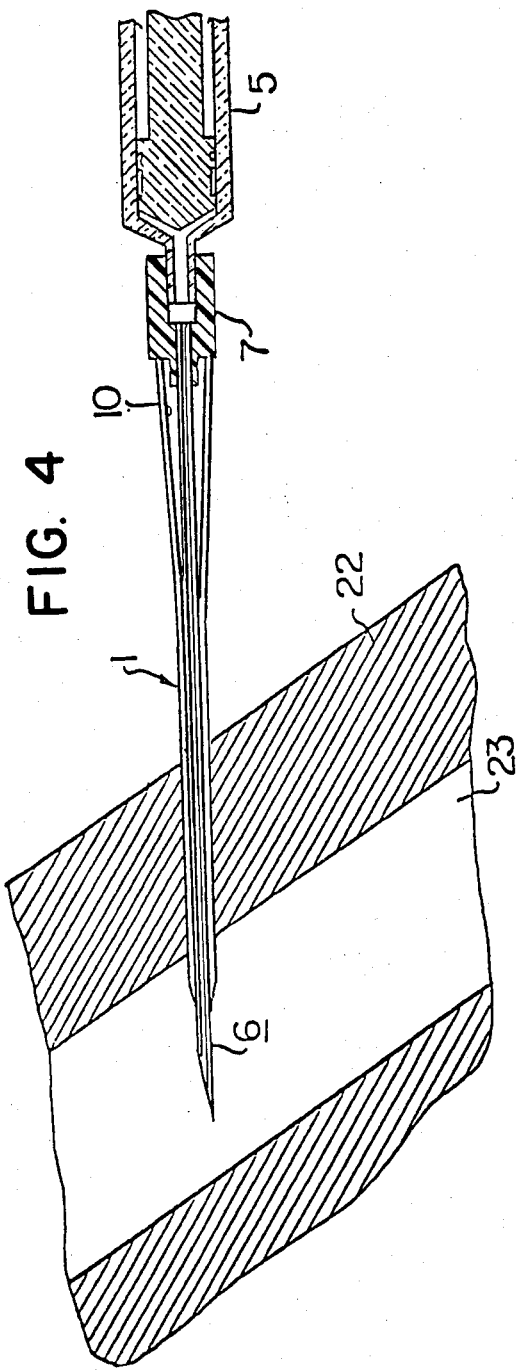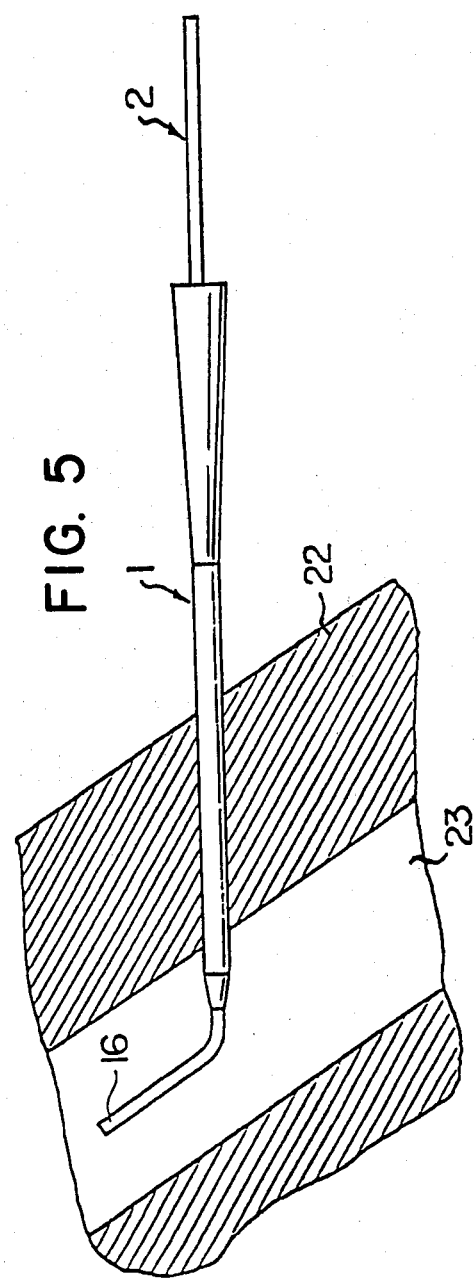

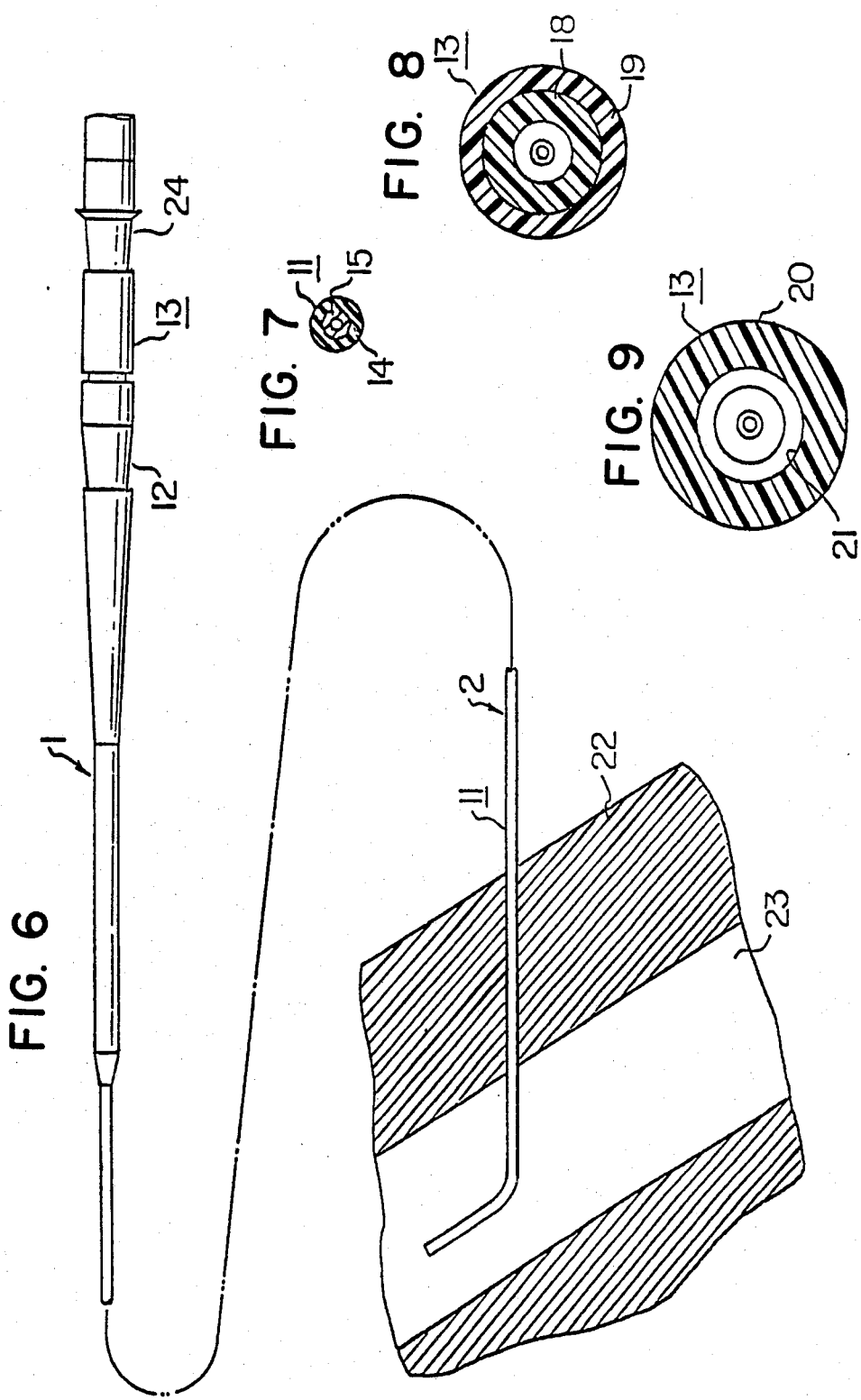

CATHETER PLACEMENT SYSTEM

BACKGROUND OF THE INVENTION

1. Field of the Invention

This invention relates generally to an improved catheter placement system and, more specifically, to an improved catheter structure.

2. Description of the Prior Art

Catheters are useful for administering fluids into the body, performing blood transfusions, removal of body fluid, blood pressure determinations, and the like.

A conventional catheter device may be put in place by any of several well known methods. In one method, the skin is cut surgically and the tip of the catheter is inserted directly into the body.

Alternatively, a needle (or cannula) is inserted into the skin and the catheter is passed through the needle to insert the catheter into the body. If the needle is left in the original position after the catheter has been inserted into the body, the catheter may be cut by the needle or there may be a risk of the needle damaging the patient's body. Therefore, the needle is usually withdrawn, leaving the catheter inserted. In order to be able to remove the needle from the external end of the catheter, a fixture having a larger size than that of the catheter must not be connected to the external end of the catheter until the needle has been removed. The needle must be removed manually, and a fitting must be subsequently installed at the external end of the catheter. Afterward, the desired instrument can be connected to the fitting.

Recently, prepackaged products which are sterilized in advance have been in demand in an effort to minimize the amount of contact with the physician. This is to minimize the contamination during the placement procedure. From this standpoint, the above-mentioned conventional methods for the insertion of catheters are not satisfactory.

In one product which has been marketed in recent years, the entire catheter device including an external fitting is sterilized and sealed in a package. When the catheter apparatus is needed, the package is opened at the end where the insertion tip of the catheter is located, and the tip is inserted into the body. The catheter is gradually inserted through a cannula directly from the package.

The cannula is always kept in its original insertion position. Thus, this apparatus has the drawback that such a cannula cannot be used in certain parts of the body. For example, the above-mentioned apparatus is not suited for insertion from the neck to the subclavian vein.

SUMMARY OF THE INVENTION

It is an object of this invention to avoid the disadvantages of the prior art.

It is also an object of this invention to place a catheter in any part of a body.

It is a further object of this invention to avoid thrombogenic irritations.

It is another object of this invention to avoid collapse of the catheter during use.

It is yet another object of the invention to remove the cannula from the body after insertion of the catheter and to hold the cannula at a convenient location.

These and other objects are accomplished by the present invention which comprises, generally speaking, an improvement in a catheter placement system. In a catheter placement system which includes a cannula; a cannula inserting device for inserting the cannula in a body, the device being adapted to be removably positioned within the cannula during insertion, the device including a needle longer than the cannula; and a catheter adapted for insertion into the body through the cannula after the cannula inserting device has been removed from the cannula; the improvement wherein the catheter comprises:

(a) a body portion having a double-wall structure consisting of an outer tube made of pliable, nonthrombogenic material and a reinforcing inner tube made from a pliable material having a rigidity which is higher than that of the outer tube and which is sufficiently high that the catheter does not collapse during use; and (b) a tip portion at one end of the body portion, the tip portion being formed from a pliable nonthrombogenic material.

In a preferred embodiment the catheter has a coupling fixture connected to the end opposite the tip portion. The coupling fixture has a tapered portion which is shaped to fit securely with the interior surface of the cannula so that when the interior surface of the cannula engages the tapered portion of the fixture, the cannula is held on the fixture.

BRIEF DESCRIPTION OF THE DRAWINGS

The invention is described below with reference to the drawings in which:

FIGS. 4–6 show schematically and in partial cross-section the method of using the catheter of the present invention.

FIGS. 7–9 show schematically and in cross-section the catheter of FIG. 3 at sections VII—VII, VIII—VIII, and IX—IX thereof.

FIGS. 1 and 2 show a catheter placement system according to the present invention. Cannula 1 consists of a thin portion 3 having a uniform diameter and an enlarged portion 4. As shown in FIG. 2, cannula 1 is attached to a cannula insertion device having a syringe 5 and a needle 6. Needle 6 is affixed to syringe 5 via connector 7. Needle 6 has a length longer than the length of cannula 1 so that when the cannula is attached to the device, the tip 8 of needle 6 extends beyond cannula 1.

The inner diameter of the thin portion of cannula 3 conforms to the outer diameter of needle 6. Needle tip 8 can be a pencil-shaped tip or a tapered tip. Considering the insertion through the skin, it is preferable to have a tapered portion at insertion end 9 opposite to enlarged portion 4 of the cannula. Enlarged portion 4 smoothly merges with thin portion 3 forming a uniform cannula. As shown in FIG. 4, interior surface 10 of enlarged portion 4 is gradually tapered until reaching the end which merges with the thin portion 3.

Figure 1:
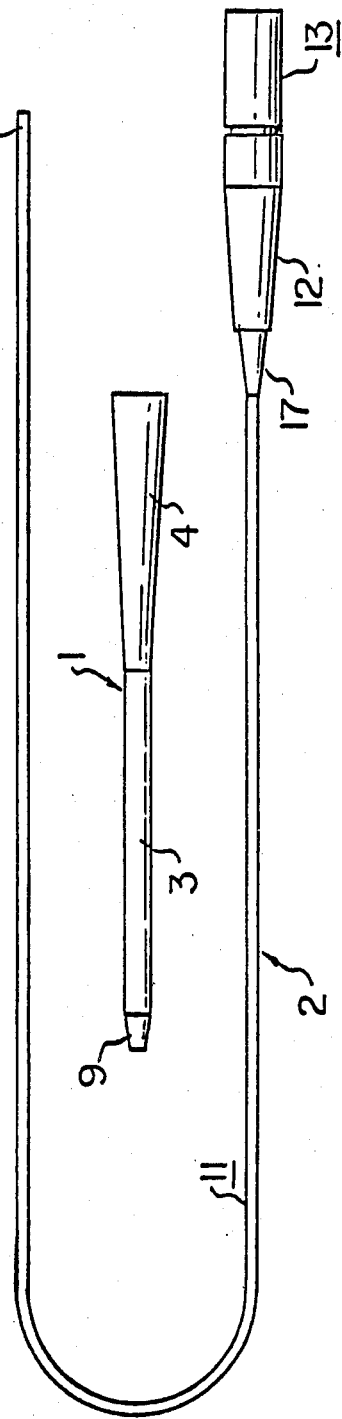
FIG. 1 shows schematically the catheter, coupling fixture and cannula.
Figure 2:
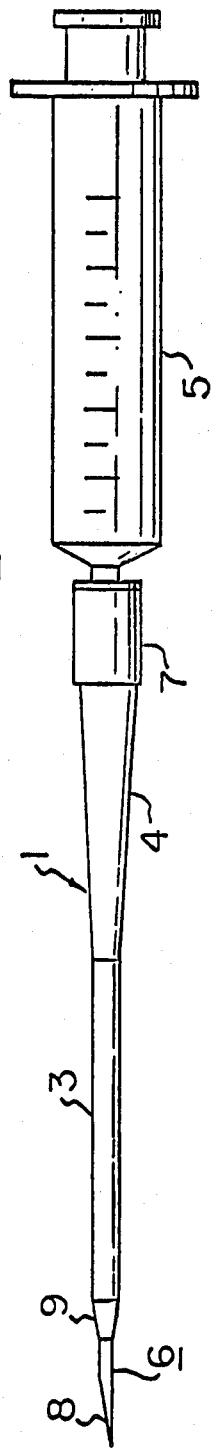
FIG. 2 shows schematically the cannula and the cannula inserting device.

Cannula 1 is fitted with needle 6 as shown in FIG. 2. Cannula 1 is made of a material having sufficient rigidity to be inserted into a patient's blood vessel through the opening made by the needle tip. Cannula 1 must have enough rigidity to withstand the pressure from the patient's skin and systemic pressure against it after the cannula insertion device is withdrawn. As long as the materials have the above-mentioned characteristics, plastics such as polypropylene and fluororesin can be used as well as metals such as stainless steel.

Figure 3:
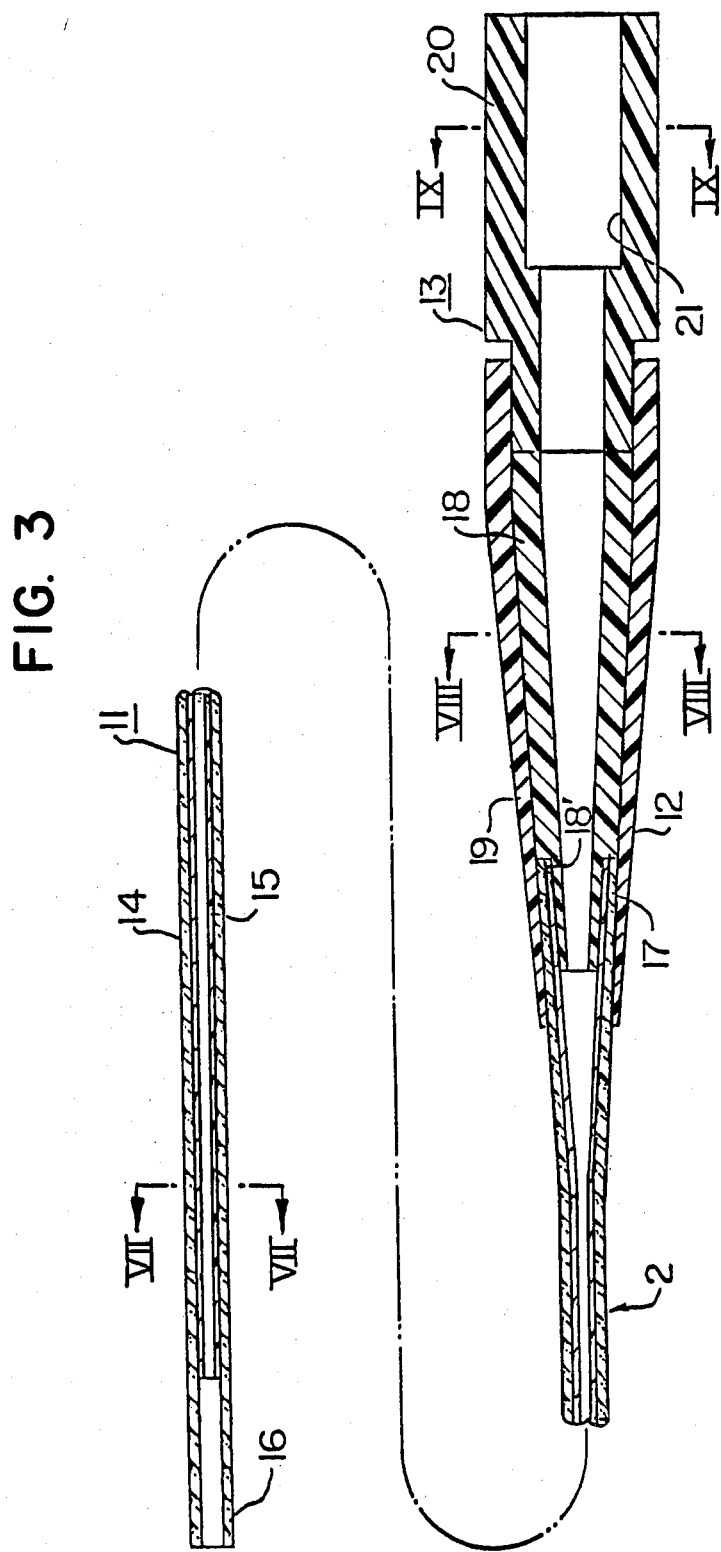
FIG. 3 shows schematically and in cross-section the cannula and the coupling fixture.

Catheter 2 consists of: a body section 11 having a substantially uniform diameter; a tip portion 16 which is connected at one end of the body section and which is inserted into the vein first; and fitting 13 which is connected to outer end 17 of body section 11. Body section 11 is gradually enlarged and is finally supported by fitting 13. An example of the construction is shown in FIG. 3.

At least body section 11 of the catheter 2, has a double-wall construction having an outer tube 14 made of pliable non-thrombogenic material such as silicone rubber, polyurethane or mixtures thereof and a reinforcing inner tube 15 made of a plastic having a higher rigidity than the outer tube 14, such as polyethylene, polyvinyl chloride, polyesters, or mixtures thereof.

Silicone rubber and polyurethane are well known nonthrombogenic materials. These materials are known for use in transfusion tubes. Although the tubes made of silicone rubber or polyurethane have the above-mentioned advantage, they have the disadvantage that they do not have sufficient firmness to be inserted easily into the body. Thus polyvinyl chloride tubes and polyethylene tubes are still commonly used for this purpose. With catheter 2 of this invention the problem is overcome by the application of a double-wall tube.

The double-wall tube consists of a nonthrombogenic material such as silicone rubber or polyurethane on the outside of the tube and a plastic material on the inside of the tube. The inner plastic material is firmer than the outer tube 14 and must have a sufficient rigidity to withstand the pressure exerted against the body section 11 of the catheter 2 when left in a vein. Therefore, the inner tube 15 is made of plastics such as polyethylene, polyvinyl chloride and polyesters. An X-ray-opaque substance such as barium sulfate can be compounded in the interior tube to form an X-ray-opaque line.

Tip portion 16 of catheter 2 can be open-ended or can be closed if holes are provided on the side wall. As shown in FIG. 3, tip portion 16 can be an extension of outer tube 14. In such a case, the irritation to the wall of the blood vessel can be reduced.

As mentioned above, outer end 17 of catheter 2 is gradually enlarged, i.e., has an inverse taper. Inverse taper end 17 is inserted into the annular groove between recessed portion 18' and 19. The groove encircles the exterior surface of inside piece 18' of fitting 13 so that end 17 is fixed at this position. A tapered portion 12 is provided on the exterior surface of outside piece 19 as the continuation of the taper provided at end 17 of the catheter. A cylindrical piece 20 is attached to the end of the outside piece 19. These pieces 18, 19 and 20 are engaged to form a uniform fitting 13. A cylindrical hole 21 is provided in cylindrical piece 20. This hole can be fitted to transfusion set, or the like. Of course, cylindrical hole 21 communicates with catheter 2. Fitting 13 is generally made of materials such as ABS resin and polyvinyl chloride. However, the materials are not limited to these types.

In the catheter apparatus of this invention, the taper angle of tapered portion 12 is an important factor. The taper angle of tapered portion 12 must be slightly greater than the taper angle of tapered interior surface 10 of enlarged portion 4 of cannula 1 as shown in FIG. 4.

After catheter 2 is inserted into the body, cannula 1 is withdrawn and the withdrawn cannula is moved upward along the catheter until tapered interior surface 10 of enlarged portion 4 of the cannula is engaged with tapered portion 12 of fitting 13. Thus, cannula 1 is fixed on the fixture.

Fitting 13 having taper portion 13 was explained above in one mode of execution, but the fitting is not limited to this mode of execution. For example, a one-piece fitting having a taper portion can be molded in advance and then the catheter tube can be attached to the fitting.

Cross-sections cut along the lines VII—VII, VIII—VIII and IX—IX in FIG. 3 are shown in FIGS. 7, 8 and 9, respectively. The size of the catheter is not limited. The outer diameter of catheter body portion 11 typically ranges from 0.5 to 5 mm and its length typically ranges from 15 to 200 cm.

The method for the application of the catheter apparatus of this invention will be described below, with reference to FIGS. 4-6. FIG. 4 shows a schematized cross-section of a patient. 22 represents the patient's skin and 23 represents the patient's vein. Cannula 1 is fitted with needle 6 of the cannula insertion device as shown in FIG. 2. The needle is used to insert cannula 1 through the skin and the wall of the vein. When tip 8 of the needle 6 reaches the vein, blood spurts through the hollow portion of the needle and the blood appears in the syringe. This phenomenon confirms that the cannula and needle have penetrated into the vein.

The cannula insertion device consisting of syringe 5 and needle 6 is then withdrawn, leaving cannula 1 in the body.

As shown in FIG. 5, the catheter 2 is inserted into the vein with the tip portion 16 being guided by cannula 1. When catheter 2 has been inserted to the desired position, cannula 1 alone is withdrawn without moving catheter 2. As shown in FIG. 6, the withdrawn cannula 1 is moved along catheter 2 until the tapered portion of the cannula is engaged with tapered portion 12 of fitting 13 attached to the other end of catheter 2. The cannula is firmly held at this position so that it does not move freely along the catheter. A commercial transfusion set or other desired instruments can be attached to fitting 13 by means of a connector 24.

The present invention has been disclosed in the above teachings and drawings with sufficient clarity and conciseness to enable one skilled in the art to make and use the invention, to know the best mode for carrying out the invention and to distinguish it from other inventions and from what is old. Many variations and obvious adaptations of the inventions will readily come to mind, and these are intended to be contained within the scope of the invention as claimed below.

That which is claimed is:

1. In a catheter placement system which includes a cannula; a cannula inserting device for inserting the cannula in a body, the device being adapted to be removably positioned within the cannula during insertion and including a needle longer than the cannula; and a catheter adapted for insertion into the body through the cannula after the cannula inserting device has been removed from the cannula; the improvement wherein the catheter comprises:

(a) a body portion having a double-wall structure consisting of an outer tube made of pliable, nonthrombogenic material and a reinforcing inner tube made from a pliable material having a rigidity which is higher than that of the outer tube and which is sufficiently high that the catheter does not collapse during use; and (b) a tip portion at one end of the body portion, the tip portion being formed from a pliable nonthrombogenic material.

2. The catheter placement system of claim 1 wherein the pliable nonthrombogenic material is made of a silicone rubber, a polyurethane or mixtures thereof.

3. The catheter placement system of claim 1 wherein the reinforcing inner tube is formed from a plastic material selected from the group consisting of polyethylene, polyvinyl chloride, polyesters and mixtures thereof.

4. The catheter placement system of claim 1 wherein the tip portion is an extension of the outer tube.

5. The catheter placement system of claim 1 wherein a coupling fixture is connected to the catheter at the end opposite the tip portion, the fixture having a tapered portion which is shaped to fit securely with the interior surface of the cannula so that when the interior surface of the cannula engages the tapered portion of the fixture, the cannula is held on the fixture.

6. The catheter placement system of claim 5 wherein the catheter is seated in an annular groove in one end of the fixture.

* * * * *